United States Patent [19]

Bartley et al.

[11] 4,065,514

[45] Dec. 27, 1977

[54] PREPARATION OF METHANE

[75] Inventors: Burton H. Bartley, Fishkill; John H. Estes, Wappingers Falls, both of N.Y.

[73] Assignee: Texaco Inc., New York, N.Y.

[21] Appl. No.: 636,237

[22] Filed: Nov. 28, 1975

Related U.S. Application Data

[63] Continuation-in-part of Ser. No. 272,528, July 17, 1972, abandoned.

[51] Int. Cl.$^2$ .............................................. C07C 9/02
[52] U.S. Cl. .............................. 260/676 R; 208/110; 208/112
[58] Field of Search ................... 208/110, 111, 112; 260/676 R; 252/460, 466 B, 472; 48/197, 213, 214, 211

[56]  References Cited

U.S. PATENT DOCUMENTS

| 2,422,670 | 6/1947 | Haensel et al. | 208/108 |
| 2,422,671 | 6/1947 | Haensel et al. | 252/459 |
| 2,734,809 | 2/1956 | Pettyjohn et al. | 48/197 R |
| 3,334,055 | 8/1967 | Dowden et al. | 252/473 |
| 3,468,641 | 9/1969 | Gross et al. | 48/213 |
| 3,625,664 | 12/1971 | Padovani | 48/213 |
| 3,644,198 | 2/1972 | Wilhelm | 208/111 |
| 3,759,823 | 9/1973 | Davies et al. | 208/138 |
| 3,825,487 | 7/1974 | Wilhelm | 208/139 |
| 3,827,867 | 8/1974 | Heinemann et al. | 48/213 |

Primary Examiner—Earl C. Thomas
Assistant Examiner—Wayne A. Langel
Attorney, Agent, or Firm—Thomas H. Whaley; Carl G. Ries; Carl G. Seutter

[57]  ABSTRACT

In accordance with certain of its aspects, this invention relates to a finely-divided, high surface area supported catalyst containing a metal of the platinum-palladium group and a metal of the iron group wherein each of said metals is substantially uniformly distributed throughout the body of said supported catalyst — and to the use of this catalyst to prepare methane by the reaction of hydrogen and hydrocarbons.

12 Claims, No Drawings

PREPARATION OF METHANE

RELATED APPLICATION

This application is a continuation-in-part of application Ser. No. 272,528 filed July 17, 1972, now abandoned.

NOVEL PROCESS

This invention relates to a process for preparing lower hydrocarbon gases such as methane from a mixture of hydrogen and hydrocarbon containing at least 2 carbon atoms. More specifically it relates to a novel catalyst useful for treating hydrocarbons to form high yields of methane.

BACKGROUND OF THE INVENTION

As is well known to those skilled in the art, various hydrocarbon streams have been treated in the presence of hydrogen (either thermally or catalytically) to produce hydrocarbons of lesser molecular weight. While it has been possible to convert hydrocarbons to selected products, it has not heretofore been commercially or economically possible to selectively convert hydrocarbons to methane in high yields.

It is an object of this invention to set forth a process for preparing lower hydrocarbons such as methane. It is another object of this invention to provide a novel catalyst particularly characterized by its high selectivity. Other objects will be apparent to those skilled in the art.

STATEMENT OF THE INVENTION

In accordance with certain of its aspects, the novel process of this invention for preparing methane by conversion of a hydrocarbon containing at least two carbon atoms may comprise contacting a mixture consisting essentially of hydrogen and said hydrocarbon with a finely-divided, high surface area catalyst containing (a) 0.01%–99.9% of total catalytic metal content of a metal of the platinum-palladium group and (b) 0.01%–99.9% of total catalytic metal content of a metal of the iron group, said iron-group metal and said platinum-palladium group metal each being substantially distributed throughout the body of said finely divided, high surface area catalyst; maintaining said mixture in contact with said catalyst at methane-preparing conditions including temperature of 300°–800° C. said hydrocarbon being converted to product gas containing methane in amount more than 50%; and withdrawing effluent gas containing product methane.

DESCRIPTION OF THE INVENTION

The hydrocarbon compounds which may be treated by the process of this invention may typically include those having more than two carbon atoms. It is a particular feature of the process of this invention that it may be used to treat a wide variety of charge hydrocarbons ranging from those having 2–6 carbon atoms up to those having high boiling points typified by naphtha, gas oil, etc. The charge hydrocarbons may include alkanes, olefins, or aromatics. Typical of the aromatic compounds which may be treated by practice of this invention may be benzene, toluene, xylene, etc. Typical of the olefin compounds which may be treated by the process of this invention may be ethylene, propylene, butylene, pentene, hexene, etc. The charge hydrocarbon compound may be a lower alkane, e.g. one having 4–10 carbon atoms. Typical of the lower alkanes, including cycloalkanes, which may be used in practice of this invention may be noted n-butane, isobutane, n-pentane, 2-methylpentane, 3-methylpentane, n-hexane, 2-methyl-n-hexane, 3-methyl-n-hexane, 2-ethyl-n-hexane, methyl cyclopropane, etc. The preferred charge hydrocarbons may include $C_4$–$C_{10}$ lower alkanes and alkenes, most preferably hexane.

In practice of the novel process of this invention, 60–200 moles, preferably 80–100 moles, say 100 moles of charge hydrocarbon may be mixed with 300–900 moles, preferably 400–600 moles, say 500 moles of hydrogen. These quantities of hydrogen may preferably correspond to about 100% of the stoichiometric amount of hydrogen required to react with the charge hydrocarbon.

This mixture of charge materials in vapor phase, hydrogen and charge hydrocarbon, may be passed into contact with the finely divided, high surface area catalyst. The preferred catalyst which may be used in practice of the process of this invention may contain (a) at least one metal of the iron group and (b) at least one metal of the platinum-palladium group. The iron group metal may contain iron, cobalt, or nickel — preferably iron. The metal of the platinum-palladium group may be platinum, palladium, iridium, rhodium, osmium, or ruthenium — preferably platinum. Typical catalyst combinations may include Fe-Pt, Co-Pd Ni-Ir, Fe-Rh, Fe-Os, Fe-Ru, Ni-Pt, Ni-Pd, Ni-Rh, Ni-Os, Ni-Ru, Co-Pt, Fe-Co-Pt, Ni-Co-Pt, Fe-Pt-Pd, Ni-Pt-Pd, etc. The preferred catalyst may be Fe-Pt iron-Platinum.

It may be possible to utilize as catalyst finely divided particles of an alloy containing a metal of the platinum-palladium group and a metal of the iron group, prepared by abrading the alloy metal to yield desired size particles or by spray cooling, or by spray condensation. It is possible to form a catalyst containing the metal components by spraying solutions of salts, either separately or in a common solution, into a drying tower.

The catalyst may be prepared in the preferred embodiment by depositing the metal on an active or an inert catalyst support. The catalyst support on which the metals may be deposited may include silica, silica-alumina, alumina, diatomaceous earth, finely divided metals such as iron, etc. The support may be of micron-size when the reaction is to be carried out in a fluidized bed or of millimeter-size when the reaction is to be carried out in a gravity-packed bed.

A preferred catalyst support may be a silica-alumina catalyst support such as that commercially available from the Davison Chemical Division of W. R. Grace under the trademark F-1-13 containing 13% alumina and 87% silica.

The catalyst may contain 0.1% – 99.9% of the platinum-palladium metal and 0.1% – 99.9% of the iron metal. Most commonly however the novel catalyst may contain 0.1 – 10 parts, preferably 0.25 – 0.75 parts, say 0.5 parts of a metal of the platinum-palladium group; 1–30 parts, preferably 2–10 parts, say 5 parts of a metal of the iron group; and in the preferred embodiment, 60–99 parts, preferably 90–98 parts, say 94.5 parts of catalyst support. A typical catalyst may include 0.5 parts of platinum, 5 parts of iron, and 94.5 parts of silica.

The catalyst may preferably be characterized by a mole ratio of iron group metal to platinum-palladium group metal of 10–80:1, more preferably 50:1. In the case of the preferred iron-platinum, the weight ratio may be 2–20:1, say about 12.5:1.

The catalyst may be prepared by impregnating catalyst support with solutions containing the metal of the iron group and the metal of the platinum-palladium group. Although it may be possible to deposit the iron group metal onto the support followed by deposit of the platinum-palladium group metal onto the iron-loaded support, or alternatively to simultaneously deposit the iron-group metal and the platinum-palladium group metal, it is found that substantially higher yields of desired product methane may be obtained if the platinum-palladium group metal is deposited first on the catalyst support, followed by the iron-group metal.

The catalyst may be prepared by impregnating catalyst support with solutions containing catalyst components. In the preferred embodiment, this may be effected by immersing 50-500 parts, preferably 80-120 parts, say 100 parts of catalyst support in 500 parts of a solution containing 0.1-10 parts, preferably 0.3-0.7 parts, say 0.5 parts of a soluble compound of the platinum-palladium group metal. Typically this compound may be a salt such as chloroplatinic acid, palladium dichloride, iridium dichloride, rhodium trinitrate, osmium dichloride, ruthenium trichloride, etc. The preferred may be a solution of chloroplatinic acid (containing 40% platinum).

The catalyst support may remain in contact with the solution for 1-4 hours, preferably 1-2 hours, say 1.5 hours at 10°-50° C, preferably 20°-30° C, say 25° C. The support particles which absorb solution during this period, may be separated and dried at 100°-140° C, preferably 105°-115° C, say 110° C for 4-24 hours, preferably 6-10 hours, say 8 hours. The catalyst particles may be calcined at 370°-550° C, preferably 450°-500° C, say 480° C for 1-4 hours, preferably 2-3 hours, say 2 hours.

The catalyst may then be cooled at 10°-40° C, preferably 20°-30° C, say 25° C. The catalyst support, loaded with platinum, may be contacted with 500 parts of solution containing a metal of the iron group. Preferably the solution may be a 1%-20%, preferably 5%-15%, say 10% solution of ferric nitrate nonahydrate. Other compounds of the iron group which may be employed include cobaltous chloride, nickel nitrate, etc.

The catalyst support may be allowed to stand in contact with this solution for 0.5-3, preferably 1-2, say 1.5 hours, with mixing, at 10°-40° C., preferably 20°-30° C., say 25° C. At the end of this time, the catalyst support may be found to have absorbed a substantial portion of the solution. The supernatant liquid may be poured off and the resultant catalyst particles may be dried in an oven for 4-24 hours, preferably 6-10 hours, say 8 hours at 95°-150° C., preferably 110°-120° C., say 120° C. The loaded catalyst particles may be calcined at 370°-550° C., preferably 450°-500° C., say 480° C for 1-4 hours, preferably 2-3 hours, say 2 hours.

Although both metals may be loaded or deposited onto the catalyst support prior to drying and calcining, the preferred embodiment is that wherein the platinum metal is deposited on the catalyst support which is then dried and calcined; and thereafter the iron metal is deposited on the catalyst support followed by further drying and calcining.

Typical catalyst composition obtained by this procedure may contain 0.2%-0.8% preferably 0.40%-0.54%, say 0.52% platinum-palladium group metal and 2%-6%, preferably 3%-5%, say 5% of the iron-group metal on inert support.

It is a feature of the novel catalyst of this invention, as will be apparent to those skilled-in-the-art on reading this description, that the catalyst composition contains each of the iron-group metals and the platinum-palladium group metals substantially distributed throughout the body of the catalyst. In a preferred embodiment for example, the catalyst may contain a support such as silica-alumina which bears a metal of the platinum-palladium group substantially uniformly distributed throughout the support and the metal of the iron-group substantially uniformly distributed throughout the support.

During the course of carrying out the process of this invention, the catalyst may normally be pretreated by reducing it for 4-24 hours, preferably 12-20 hours, say 16 hours at 300°-550° C., preferably 400°-500° C., say 462° C. with hydrogen gas. In the preferred embodiment, the iron may be in the form of ferrous iron; and more preferably, it may be reduced to metallic iron.

Practice of this invention may be carried out by passing the charge mixture of hydrogen and hydrocarbon into contact with the catalyst. The reaction may be carried out in vapor phase out at 300°-800° C., preferably 450°-550° C., say 500° C, at pressure of 0-1000 psig, preferably 400-600 psig, sayd 500 psig.

During the reaction, the charge mixture of hydrogen and hydrocarbon may be admitted to the catalyst bed at a rate of 0.01-10.0, preferably 0.5-4, say 1 part of charge mixture per hour per part of catalyst.

It will be apparent that the reaction which may be carried out during practice of the process of this invention may include the following.

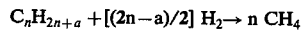
$$C_nH_{2n+a} + [(2n-a)/2]\ H_2 \rightarrow n\ CH_4$$

wherein $|a/2|$ is an integer less than 2. It will be apparent that $a$ may be equal to minus 2, zero, or plus 2.

When $a$ is $-2$, the reaction may be:

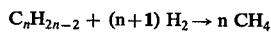
$$C_nH_{2n-2} + (n+1)\ H_2 \rightarrow n\ CH_4$$

or typically, when $n$ is 6,

$$C_6H_{10} + 7\ H_2 \rightarrow 6\ CH_4$$

When $a$ is zero, the reaction may be:

$$C_nH_{2n} + n\ H_2 \rightarrow n\ CH_4$$

or typically, when $n$ is 6,

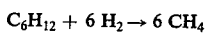
$$C_6H_{12} + 6\ H_2 \rightarrow 6\ CH_4$$

When $a$ is $+2$, the reaction may be:

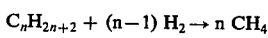
$$C_nH_{2n+2} + (n-1)\ H_2 \rightarrow n\ CH_4$$

or typically, when $n$ is 6,

$$C_6H_{14} + 5\ H_2 \rightarrow 6\ CH_4$$

It is a feature of this invention in accordance with certain of its aspects that the hydrogen gas may be continuously passed through the catalyst bed and the charge hydrocarbon may be added to the stream of hydrogen gas from time to time as by a pulse addition. Alternatively the charge hydrocarbon may be added continuously to the continuously flowing stream of hydrogen.

It is also a feature of this invention that at the temperature of the reaction, all of the hydrocarbon charge material which reacts in the presence of the catalyst, may be substantially completely converted to methane gas. Commonly, it may be found that 50%–100%, preferably 90%–100%, say 100% of the charge hydrocarbon may be converted to products; and of the converted products so obtained, 50%–100%, preferably 90%–100%, say 100% may be methane.

DESCRIPTION OF THE PREFERRED EMBODIMENTS

Practice of the process of this invention may be observed from the following illustrative examples wherein as elsewhere in this specification, all parts are parts by weight unless otherwise noted.

EXAMPLE I

In this example, which illustrates preferred practice of the invention, the catalyst support included 94 parts by weight of silica-alumina (commercially available under the trademark F-1-13 sold by the Davison Chemical Division of W. R. Grace & Company). The catalyst support particles had an average particle size of 59 microns and 99% was less than 150 microns. It contained 13% $Al_2O_3$ and 86.8% $SiO_2$.

100 parts of catalyst support were added to aqueous solution containing 500 parts of water and 1.9 parts of chloroplatinic acid. The mixture was allowed to stand for 1.5 hours and the liquid was poured off. The solid catalyst support containing platinum was dried for 8 hours at 110° C. and calcined for 2 hours at 480° C. The platinum-containing catalyst at 25° C was then added to an aqueous solution containing 450 parts of water and 50 parts of ferric nitrate. The mixture was thoroughly agitated and the components allowed to stand for one hour. At end of this period, the liquid was poured off and the solid catalyst was dried for 8 hours at 120° C. It was then pretreated at 450° C. for 2 hours in air. The soprepared catalyst contained 5% iron and 0.75% platinum on silica-alumina.

In this example, 0.595 parts of catalyst were placed in a reactor. Hydrogen was passed through the system at a flow rate of about 1 ml per second. Prior to beginning the run, the catalyst was pretreated by reducing it for 16 hours at 464° C. in the presence of hydrogen.

The charge hydrocarbon used in this example was impure n-hexane containing 85% n-hexane, 5% 3-methylpentane, 10% $C_7$ isomer, and a trace of 2-methylpentane. This impure charge n-hexane, in amount of 3 micromoles per sample, was pulsed into the flowing stream of hydrogen. The reaction mixture was passed into intimate contact with the iron-platinum catalyst. During the course of the reaction at ca. 0 psig, the catalyst temperature was maintained at 340° C. The effluent gas from the catalyst chamber was analyzed to determine the content of methane therein.

In this reaction carried out at 340° C., 100% of charge n-hexane reacted; and 97% of the product gas mixture was methane.

EXAMPLE II

The process of Example I was duplicated except that the temperature of reaction was lowered to 300° C. 66% of the charge n-hexane was converted; and the effluent gas contained 25% methane.

EXAMPLE III

The procedure of Example I was duplicated except that the charge hydrocarbon was isobutane in place of n-hexane. The temperature of reaction was 300° C. Analysis of the effluent gas from the reaction indicated that 66% of the charge isobutane has been converted to methane; and substantially no (i.e. less than 2%) ethane or propane had been formed.

EXAMPEL IV

The procedure of Example I was duplicated except that the charge hydrocarbon was n-butane in place of n-hexane. The temperature of reaction was 300° C. Analysis of the effluent gas from the reaction indicated that 66% n-butane had been converted to methane; and substantially no (i.e. less than 2%) ethane or propane had been formed.

EXAMPLE V

The procedure of Example I was duplicated except that the catalyst support was silica and the charge hydrocarbon was benzene. The temperature of reaction was 300° C. Analysis of the effluent gas from the reaction indicated that 100% of the benzene had been converted; and the effluent gas contained 100% methane with less than 2% of other decomposition products.

EXAMPLE VI

The procedure of Example I was duplicated except that the charge hydrocarbon was methylcyclopropane. The temperature of reaction was 300° C. Analysis of the effluent gas from the catalytic reactor contained only desired methane product together with unreacted methylcyclopropane.

EXAMPLE VII

In this example which serves as a control example, the procedure of Example I was duplicated except that the charge was pure n-hexane and that in the preparation of the catalyst, the platinum component was omitted i.e. the catalyst used contained no platinum and 5% iron on an inert catalyst support. The effluent gas from the catalytic reaction contained charge hydrocarbon and above 5% methane. This is regarded as unsatisfactory.

EXAMPLE VIII

In this control example, the procedure of Example I was duplicated except that the charge was pure n-hexane and that the catalyst contained 0.75% platinum (and no iron) on inert silica support. It was found that the use of this platinum-containing catalyst permitted conversion only of 96% of the charge n-hexane. However, it wa noted that the amount of methane found in the effluent product was only 20%. By comparison with Example I, it may be seen that this catalyst may not be satisfactory for carrying out the process of the instant invention.

EXAMPLE IX

In this example, the procedure of Example I was carried out except that the charge was pure n-hexane and that the support for the iron-platinum catalyst was silica. The silica support was the Davison Chemical Division 926 brand of silica catalyst having a surface area of about 470 square meters per gram.

Passage at 302° C. and 0 psig of a hydrogen stream containing n-hexane over the catalyst yielded a product gas containing substantially only methane as the decomposition product of the n-hexane.

From these last three examples, will be apparent that the use of the novel catalyst composition of this invention permits attainment of selective and high yields of methane; use of catalyst containing either iron alone or platinum alone does not yield desired product in substantial yield.

Results comparable to the above may be obtained by the use of 0.5% palladium – 5% iron on silica; 0.40% palladium – 4.5% cobalt on silica-alumina; 0.45% platinum–0.5% iridium—5% nickel, etc.

EXAMPLES X - XXI

In the following series of examples, the catalyst was prepared in a manner to demonstrate the effect of (a) adding the platinum to the catalyst support prior to the addition of iron, (b) adding the iron to the catalyst support prior to the addition of platinum, and (c) adding the platinum and iron together.

In each of the examples, the catalyst was prepared by using a catalyst support of silica (Davison 926 brand) of 20–40 mesh size. The iron component was added in the form of a measured amount (sufficient to give the final content) of an aqueous solution of ferric nitrate; the platinum was added in the form of a measured amount (sufficient to give the final content) of an aqueous solution of chlorplatinic acid.

The catalyst and added solution(s) were dried overnight at 120° C and calcined in air at 485° C for 2 hours. When the two metals were added simultaneously, drying and calcining followed the addition. In those cases in which the metals were added simultaneously, the catalyst (after addition of both metals) was dried and calcined as noted.

In this series of runs, 0.5313± 0.008g of catalyst at 300° ± 1° C is maintained in a reactor through which hydrogen gas flows at 60 ml/min. The catalyst, prior to use, is pretreated by reducing the flowing hydrogen at 450° C for 16 hours. Reactant n-hexane is pulsed into the reactor in amounts of 2.7 micromole amounts per pulse and the reactant is in contact with the catalyst for about two seconds.

The product gas is cooled in a liquid nitrogen trap which removes all products except methane and hydrogen; and the gas is analyzed for methane. The results of the series of examples may be observed from the following table:

TABLE

| Example Number | Order of Addition of Metal | Pt Wt. % | Fe Wt. % | Product Gas, Methane % |
|---|---|---|---|---|
| X | Pt, then Fe | 0.71 | 4.79 | 54.6±2.5 |
| XI | Pt, then Fe | 0.20 | 4.71 | 82.3±4.9 |
| XII | Fe, Pt together | 0.67 | 4.79 | 23.9±4.1 |
| XIII | Fe, then Pt | 0.67 | 4.70 | 12.8±3.2 |
| XIV | Fe only | 0 | 4.98 | 23.0±3.1 |
| XV | Pt, then Fe | 0.14 | 4.62 | 69.6±8.8 |
| XVI | Pt, then Fe | 0.25 | 4.63 | 83.6±8.5 |
| XVII | Pt, then Fe | 0.70 | 4.94 | 70.9±1.5 |
| XVIII | Pt, then Fe | 0.77 | 4.74 | 35.9±1.4 |
| XIX | Pt, Fe together | 0.67 | 4.86 | 36.7±1.5 |
| XX | Fe, then Pt | 0.65 | 4.63 | 22.8±4.4 |
| XXI | Fe, then Pt | 0.29 | 4.79 | 32.6±2.6 |

The wt. % Pt and Fe are on a dry basis. The methane value is carbon atom percent of methane in the product gas.

From the above Table, it will be apparent that the catalyst of this invention permits attainment of product gas containing up to eg 83.6% methane. As may be noted, the use of a catalyst prepared by first placing the platinum on the catalyst support and thereafter the iron on the support (Examples X, XI, XV, XVI, XVII, and XVIII) gives a product gas containing more methane than is obtained by use of a catalyst wherein the iron is placed on the support before the platinum (Examples XIII, XX, and XXI) or a catalyst wherein the iron and platinum are added simultaneously (Example XII and XIX), or a catalyst wherein only iron is present (Example XIV) the latter giving a product containing only one-third or less methane than may be obtained by this invention eg Example XI.

It will also be apparent that when the iron is added to the silica prior to the platinum, the maximum content of methane (about 33%) may be obtained when the platinum content of the catalyst is about 0.5%. In the preferred embodiment, when the platinum is added to the silica prior to the iron, the maximum content of methane (about 97%) is obtained when the platinum content of the catalyst is about 0.5%. The graphs plotted from these Examples, reveals that the maximum catalytic activity is achieved when the platinum content is 0.25%–0.70%, preferably about 0.50%.

EXAMPLE XXII

In this example, the catalyst was platinumcobalt catalyst on Davison 926 brand silica catalyst support, prepared as in the procedure of Example I except for the substitution of cobalt nitrate (for the ferric nitrate) and for the use of silica catalyst support in place of the silica-alumina catalyst support. Prior to the run, the catalyst was reduced for 18 hours in flowing hydrogen at 462° C.

The temperature of reaction in three runs were 351° C, 300° C, and 260° C. The charge stream was n-hexane in amount of 2.7 micromoles per sample pulsed into flowing hydrogen. The product stream was analyzed for mole percent of methane, mole percent of n-hexane unreacted, and mole percent of other products. The results are set forth in the following table:

TABLE

| Reaction Temperature ° C | Mole % Methane | Mole % Unreacted n-hexane | Mole % other products |
|---|---|---|---|
| 351 | 97 | 0 | 3 propane |
| 300 | 89 | 0 | 11 propane |
| 260 | 84 | 1 | 16 $C_3$, $C_4$, $C_5$ paraffins |

EXAMPLE XXIII

In this example, the catalyst was 0.75% palladium—5% iron catalyst on Davison 926 brand silica catalyst support, prepared in manner comparable to that of Example XXII.

At 398° C, 2.8 micromoles of n-hexane were pulsed into hydrogen carrier stream; the effluent gas contained 34 mole % of methane, 2 mole % of $C_2$ through $C_6$ products, and 64 mole % of unreacted n-hexane. Thus 94% of the hexane reacted was converted to methane.

From inspection of Examples I–XXIII, it will be apparent that superior results are readily attained by the use of the novel catalyst of this invention in which the catalyst contains in each instance a metal of the platinum-palladium group which is substantially uniformly distributed throughout the body of the finely divided catalyst and a metal of the iron-group which is substantially uniformly distributed throughout the body of the finely divided catalyst — and the catalyst is thus substantially homogeneous with respect to concentrations of each of the two metals.

It is particularly unexpected to find that in typical instances, it may readily be possible to carry out the process of this invention at 50%–100%, preferably 90%–100% say 100% conversion and 50%–100%, preferably 90%–100%, say 100% selectivity — which may correspond to yields of 25%–100%, preferably 81%–100%, say 100% yield.

The catalyst mass may include particles of varying shapes including balls, cylinders, or particles of random configuration. Although the particles may have an average diameter of 0.01–10 mm, they may preferably have a diameter of 1–5 mm, say 3 mm.

It will be apparent to those skilled in the art that this invention has been described with respect to specific embodiments; and numerous changes and modifications will be apparent which fall within the scope of this invention.

We claim:

1. The process for preparing methane by conversion of a hydrocarbon containing at least two carbon atoms which comprises contacting in a conversion zone a mixture consisting essentially of hydrogen and said hydrocarbon with a finely-divided, high surface area catalyst consisting essentially of (a) 0.01%–99.9% of total catalytic metal content of a metal of the platinum-palladium group and (b) 0.01%–99.9% of total catalytic metal content of a metal of the iron group, said iron-group metal and said platinum-palladium group metal, each being substantially distributed throughout the body of said finely divided, high surface area catalyst; maintaining said mixture in contact with said catalyst at methane-preparing conditions including temperature of 300°–800° C, and withdrawing effluent gas containing product methane in amount more than 50% by weight from said conversion zone.

2. The process for preparing methane as claimed in claim 1 wherein said catalyst is mounted on a support.

3. The process for preparing methane as claimed in claim 2 wherein the hydrocarbon is hexane and the iron group and platinum-palladium group metals are mounted on a silica-alumina catalyst support.

4. The process for preparing methane as claimed in claim 1 wherein said hydrocarbon is a lower alkane.

5. The process for preparing methane as claimed in claim 1 wherein said hydrocarbon is selected from the group consisting of heptane, hexane, isobutane, n-butane, benzene, and methylcyclopropane.

6. The process for preparing methane as claimed in claim 1 wherein said hydrocarbon is hexane.

7. The process for preparing methane by conversion of a hydrocarbon containing at least two carbon atoms which comprises contacting in a conversion zone a mixture consisting essentially of hydrogen and said hydrocarbon with a finely-divided, high surface area catalyst consisting essentially of (a) 0.01%–99.9% of total catalytic metal content of a metal of the platinum-palladium group and (b) 0.01%–99.9% of total catalytic metal content of a metal of the iron group; maintaining said mixture in contact with said catalyst at methane-preparing conditions including temperature of 300°–800° C, said hydrocarbon being converted to product methane in amount more than 50%, said catalyst having been prepared by contacting finely-divided, high surface area catalyst support with a solution of a soluble copound of a metal of the platinum-palladium group thereby distributing said platinum-palladium group metal substantially throughout the body of said catalyst support, drying said catalyst support bearing said metal of the platinum-palladium group, calcining said catalyst support bearing said metal of the platinum-palladium group, contacting said calcined support bearing said metal of the platinum-palladium group with a solution of a metal of the iron group thereby distributing said metal of the iron group substantially throughout the body of said catalyst support, drying said catalyst support bearing said metal of the iron group, and calcining said catalyst support bearing said metal of the iron group; and withdrawing effluent gas containing product methane in amount more than 50% by weight from said conversion zone.

8. The process for preparing methane as claimed in claim 7 wherein said catalyst consists essentially of iron and platinum on a support.

9. The process for preparing methane as claimed in claim 7 wherein 90%–100% of said hydrocarbon is converted to methane.

10. The process for preparing methane as claimed in claim 7 wherein said metal of the iron group is in metallic form.

11. The process for preparing methane by conversion of a hydrocarbon containing at least two carbon atoms which comprises contacting in a conversion zone a mixture consisting essentially of hydrogen and said hydrocarbon with finely-divided, high surface area catalyst including a catalyst support on which is deposited 0.01%–99.9% of total catalytic metal content of a metal of the platinum-palladium group and, deposited on said catalyst support bearing said platinum-palladium metal, 0.01%–99.9% of total catalytic metal content of a metal of the iron group, said catalyst consisting essentially of catalyst support and said iron group metal and said platinum-palladium group metal each of which is substantially distributed through the body of said finely divided, high surface area catalyst; maintaining said mixture in contact with said catalyst at methane-preparing conditions including temperature of 300°–800° C, and withdrawing effluent gas containing product methane in amount more than 50% by weight from said conversion zone.

12. The process for preparing effluent gas containing substantial proportions of methane by conversion of a lower alkane hydrocarbon containing at least two carbon atoms which comprises contacting in a conversion zone a mixture consisting essentially of hydrogen and said lower alkane hydrocarbon with a high surface area catalyst consisting essentially of (a) 0.01%–99.9% of total catalytic metal content of a metal of the platinum-palladium group and (b) 0.01%–99.9% of total catalytic metal content of iron, each of said platinum-palladium group metal and said iron being substantially distributed through the body of catalyst; maintaining said mixture in contact with said catalyst at methane-preparing conditions including temperature of about 300° C; and withdrawing effluent gas containing methane in amount more than 50% by weight from said conversion zone.

* * * * *